United States Patent
Nesvadba et al.

(10) Patent No.: US 9,127,098 B2
(45) Date of Patent: Sep. 8, 2015

(54) O-IMINO-ISO-UREA COMPOUNDS AND POLYMERIZABLE COMPOSITIONS THEREOF

(71) Applicant: BASF SE, Ludwigshafen (DE)

(72) Inventors: Peter Nesvadba, Marly (CH); Lucienne Bugnon Folger, Pfeffingen (CH); Antoine Carroy, Limburgerhof (DE); Marc Faller, Hegenheim (FR); Bruno Spony, Wahlbach (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/135,788

(22) Filed: Dec. 20, 2013

(65) Prior Publication Data

US 2014/0113987 A1   Apr. 24, 2014

Related U.S. Application Data

(62) Division of application No. 13/319,244, filed as application No. PCT/EP2010/056063 on May 5, 2010, now Pat. No. 8,664,288.

(30) Foreign Application Priority Data

May 7, 2009   (EP) ..................................... 09159604
May 7, 2009   (EP) ..................................... 09159664

(51) Int. Cl.
  *C08F 2/46* (2006.01)
  *C08F 2/50* (2006.01)
  *B29C 71/04* (2006.01)
  *A61L 2/08* (2006.01)
  *A61L 24/00* (2006.01)
  *C08G 61/04* (2006.01)
  *C08F 120/18* (2006.01)
  *C07C 275/70* (2006.01)
  *C08F 4/00* (2006.01)
  *C07C 251/58* (2006.01)
  *C08F 8/32* (2006.01)
  *C09D 135/02* (2006.01)

(52) U.S. Cl.
  CPC ............. *C08F 120/18* (2013.01); *C07C 251/58* (2013.01); *C07C 275/70* (2013.01); *C08F 4/00* (2013.01); *C08F 8/32* (2013.01); *C09D 135/02* (2013.01); *C07C 2101/14* (2013.01); *C07C 2101/20* (2013.01)

(58) Field of Classification Search
  CPC ....... C08F 120/18; C08F 8/32; C07C 251/58; C09D 135/02
  USPC .................................................. 522/28; 520/1
  See application file for complete search history.

(56) References Cited

U.S. PATENT DOCUMENTS

| | | | | | |
|---|---|---|---|---|---|
| 2,654,725 | A | * | 10/1953 | Price | 526/302 |
| 5,166,394 | A | * | 11/1992 | Breipohl et al. | 558/301 |
| 2006/0128903 | A1 | | 6/2006 | Roth et al. | |
| 2006/0172080 | A1 | | 8/2006 | Wolf et al. | |
| 2008/0132600 | A1 | | 6/2008 | Nesvadba et al. | |

FOREIGN PATENT DOCUMENTS

| WO | 01 90113 | 11/2001 |
|---|---|---|
| WO | 2004 081100 | 9/2004 |
| WO | 2006 051047 | 5/2006 |

OTHER PUBLICATIONS

Radau et al , Addition von Oximen an Carbodiimide unter Tetrafluorborsaure-Katalyse, Sep. 24, 1971, Arch. Phamarz., 702-707).*
Office Action issued Jan. 9, 2014 in Japanese Patent Application No. 2012-509020 (English translation only).
Radau, M. et al., "Addition von Oximen an Carbodiimide unter Tetrafluorborsaure-Katalyse", Archiv Der Pharmazie, vol. 305, pp. 702-707, XP-002547647, (1972).
Schmidt, E. et al., "Zur Kenntnis Aliphatischer Carbodiimide", Justus Liebigs Annalen Der Chemie, vol. 639, pp. 24-31, XP-002547648, (1961).
International Search Report Issued Aug. 11, 2010 in PCT/EP10/056063 filed May 5, 2010.
Office Action issued Dec. 9, 2014, in Russian Patent Application No. 2011149550/04(074356).
STN data base, registration No. RN 408532-87-6, entry date Apr. 29, 2002.

* cited by examiner

*Primary Examiner* — Ling Choi
*Assistant Examiner* — Jessica E Whiteley
(74) *Attorney, Agent, or Firm* — Oblon, McClelland, Maier & Neustadt, L.L.P.

(57) ABSTRACT

The invention relates to the use of O-imino-iso-urea compounds as source of radicals to polymerizable compositions comprising these O-imino-iso-urea and to new O-imino-iso-urea compounds. The O-Imino-isoureas compounds are compounds of the formula (I)

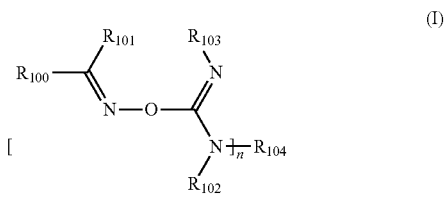

wherein
and salts thereof.

6 Claims, No Drawings

O-IMINO-ISO-UREA COMPOUNDS AND POLYMERIZABLE COMPOSITIONS THEREOF

CROSS REFERENCE TO RELATED APPLICATION(S)

This application is a divisional of U.S. application Ser. No. 13/319,244, filed on Jan. 13, 2012, which is a 35 U.S.C. §371 national stage patent application of international patent application PCT/EP10/056063, filed on May 5, 2010, the text of which is incorporated by reference, and claims foreign priority to EPO 09159664.3 filed on May 7, 2009 and EPO 09159604.9 filed on May 7, 2009, the entire content of which is incorporated herein by reference.

The invention relates to the use of O-imino-iso-urea compounds as source of radicals in particular as polymerization initiators, to polymerizable compositions comprising these O-imino-iso-urea and to new O-imino-iso-urea compounds.

Free-radical polymerization belongs to the most important polymerization methods. It is used for preparing many commercially important polymers such as polystyrene, PVC, polyacrylates, polymethacrylates, PAN and other polymers. For technical details, reference may be made to the still relevant standard work G. Odian, Principles of Polymerization, McGraw-Hill New York 1991.

Free-radical polymerizations are started using initiators. Examples of initiators which have become established in polymer technology are azo compounds, dialkyl peroxides, diacyl peroxides, hydroperoxides, thermolabile C—C-dimers, redox systems and photoinitiators. Reference is made to the "Handbook of Free Radical Initiators", (E. T. Denisov, T. G. Denisova, T. S. Pokidova, J. Wiley & Sons, Inc. Hoboken, N.J., 2003).

Despite their widespread use, the known polymerization initiators have various disadvantages. Thus, for example, peroxides are extremely readily ignitable and sustain fire and present thus potential explosion hazards, so that their manufacture, storage, transport and use has to involve costly safety precautions. Some initiators further generate toxic products, as e.g. AIBN.

There is therefore a general need for new initiators for free-radical polymerization processes which have a satisfactory safety profile.

M. Radau and K. Hartke describe in "Archiv der Pharmazie" Vol. 305, 1972, pages 702-707 the addition of oximes to carbodiimide. The use as polymerization initiator is not described.

Erich Schmidt et al describe in "Justus Liebigs Annalen der Chemie" Vol. 639, 1961, pages 24-31 O-imino-isourea compounds prepared by reacting methyl tert. butyl-carbodiimide or diisopropyl carbodiimide with methylisopropylketoxim. The use as polymerization initiator is not described.

WO 2001/90113 and WO 2004/081100 describe sterically hindered N-acyloxyamines as a new class of polymerization initiators.

Further new polymerization initiators N-substituted imides are described in WO 2006/051047 O-dialkylamino-isoureas PCT/EP200906794 (filed Dec. 28, 2009) and aryltriazenes EP 09156625.7 (filed Mar. 30, 2009).

We have now discovered that O-imino-isoureas available for example via reaction of carbodiimides with oximes are very efficient initiators of free radical polymerization or of other processes which are triggered off by free radicals, for example controlled degradation of polyolefines or for crosslinking processes. Furthermore, many of these O-imino-isoureas are novel compounds.

The object of the invention is the use of O-imino-isoureas compounds of the general formula (I) as source of radicals, particular as polymerization initiators

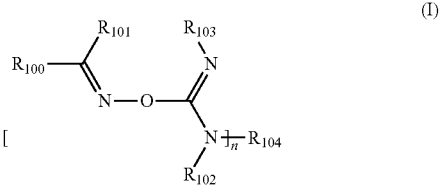

(I)

wherein n is 1, 2, 3 or 4, $R_{100}$ and $R_{101}$ are independently H, $C_{1-18}$ alkyl, $C_3$-$C_{12}$cycloalkyl, $C_6$-$C_{14}$aryl, $C_1$-$C_{14}$heteroaryl, $C_7$-$C_{15}$aralkyl, $C_2$-$C_{14}$heteroaralkyl, cyano, or $R_{100}$ and $R_{101}$ form together with the carbon to which they are attached a mono or polycyclic $C_3$-$C_{18}$ carbocyclic or $C_1$-$C_{18}$ heterocyclic ring;

$R_{102}$ and $R_{103}$ are independently $C_1$-$C_{18}$alkyl, $C_3$-$C_{12}$cycloalkyl, $C_6$-$C_{14}$aryl, $C_6$-$C_{14}$aryl once or more than once substituted by $C_1$-$C_{18}$alkyl; $C_7$-$C_{15}$aralkyl, $(CH_3)_3Si$—; or $R_{102}$ and $R_{103}$ are $C_1$-$C_{18}$alkyl, $C_3$-$C_{12}$cycloalkyl, $C_6$-$C_{14}$aryl, $C_7$-$C_{15}$aralkyl or $R_{102}$ and $R_{103}$ are $C_1$-$C_{18}$alkyl, $C_3$-$C_{12}$cycloalkyl which are interrupted or substituted by O or by N containing groups selected from $C_1$-$C_{18}$alkylamino, bis($C_1$-$C_{18}$alkyl)amino or tris($C_1$-$C_{18}$alkyl)ammonium;

$R_{104}$ if n is 1 is H, $C_1$-$C_{18}$alkyl, $C_3$-$C_{12}$cycloalkyl, $C_7$-$C_{14}$aralkyl, $C_6$-$C_{14}$aryl or acyl selected from the group consisting of the following acyls —C(=O)—H, —C(=O)—$C_1$-$C_{18}$alkyl, —C(=O)—$C_2$-$C_{18}$alkenyl, —C(=O)—$C_6$-$C_{14}$aryl, —C(=O)—$C_2$-$C_{18}$alkenyl-$C_6$-$C_{14}$aryl, —C(=O)—O—$C_1$-$C_{18}$alkyl, —C(=O)—O—$C_6$-$C_{14}$aryl, —C(=O)—NH—$C_1$-$C_{18}$alkyl, —C(=O)—NH—$C_6$-$C_{14}$aryl and —C(=O)—N($C_1$-$C_{18}$alkyl)$_2$; or $R_{102}$ and $R_{104}$ if n is 1 form together with the nitrogen atom to which they are attached a 5 to 12 membered ring which my contain additional heteroatoms, $R_{104}$ if n is more than 1 is di-, tri-, tetra-$C_1$-$C_{18}$alkylidene, diacyls, triacyls or tetraacyls and salts thereof.

Examples of such rings $R_{102}$-$R_{104}$ are: pyrrolidine, piperidine, morpholine, piperazine, N-methyl-piperazine, hexamethyleneimine.

The structure of (I) can be such (e.g. dimeric, trimeric, oligomeric or polymeric) that the molecule (I) contains the isourea fragment more than once, for example 2 to 10 times.

Preferred is a monomeric structure (n is 1); a dimeric structure (n=2), or a trimeric structure n=3.

The compounds (I) are suitable as polymerization initiators of free radical polymerization, particularly for use in polymerization processes to prepare coatings. Thermal curing and dual curing processes are encompassed, especially those in which the second curing process is triggered by electromagnetic or actinic radiation, for example by light, near infrared radiation or electron beam.

Furthermore, these compounds (I) are suitable for other processes which are triggered off by free radicals, for example, controlled degradation of polyolefines.

Furthermore these compounds (I) are suitable for crosslinking unsaturated polymer resins.

The crosslinking process comprises heating the unsaturated polymer resin together with the compounds (I).

The term polymer encompasses oligomers, cooligomers, polymers and copolymers, for example, random block, multiblock, star or gradient copolymers.

Definition of the Radicals

The residue 'alk' or 'cycloalk' is used in combination with standard IUPAC terminology.

'alkene' is standing for residues comprising one or more double bonds as well as optionally single bonds however excluding aromatic residues and 'alkine' standing for residues comprising one or more triple bonds as well as optionally single and/or double bonds, the maximal number of double and triple bonds in said residue 'alkene' or 'alkine' being totally no more than one half of the number of C atoms in said residue alkene' or 'alkine'.

$C_1$-$C_{18}$alkyl in the compound of formula I is, for example, $C_1$-$C_6$alkyl, e.g. methyl, ethyl, n-propyl or isopropyl or n-, sec- or tert-butyl or straight-chain or branched pentyl or hexyl, or $C_7$-$C_{19}$alkyl, e.g. straight-chain or branched heptyl, octyl, isooctyl, nonyl, tert-nonyl, decyl or undecyl, n-tridecyl, n-tetradecyl, n-hexadecyl or n-octadecyl.

The $C_1$-$C_{18}$alkyls and $C_3$-$C_{12}$cycloalkyls in the groups $R_{101}$-$R_{104}$ of compound of formula I may also be substituted by suitable substituents, e.g. $C_1$-$C_4$alkoxy, or halogen, e.g. chlorine or fluorine $C_2$-$C_{18}$alkenyl is for example ethenyl, propenyl, butenyl, pentenyl, hexenyl, heptenyl, octenyl, dodecenyl and the like including their isomers.

$C_6$-$C_{14}$Aryl, $C_7$-$C_{15}$aralkyl, $C_1$-$C_{14}$heteroaryl and $C_2$-$C_{24}$heteroaralkyl can be mono- or polycyclic, condensed or conjugated, or two or more aromatic or heteroaromatic groups may be bridged with an alkylene group. $C_6$-$C_{14}$Aryl, $C_7$-$C_{15}$aralkyl, $C_1$-$C_{14}$heteroaryl or $C_2$-$C_{14}$heteroaralkyl are for example phenyl, benzyl, naphthyl, indyl, indenyl, fluorenyl, acenaphthyl, biphenylyl, anthracyl, o-, m- or p-terphenyl.

$C_6$-$C_{14}$aryl is, for example, carbocyclic monoaryl or diaryl, preferably monoaryl, e.g. phenyl, which may be monosubstituted or disubstituted by suitable substituents, e.g. $C_1$-$C_4$alkyl, e.g. methyl, ethyl or tert-butyl, $C_1$-$C_4$alkoxy, e.g. methoxy or ethoxy, or halogen, e.g. chlorine. In the case of disubstitution, the 2- and 6-positions are preferred.

$C_6$-$C_{14}$aryl once or more than once substituted by $C_1$-$C_{18}$alkyl is for example phenyl once or twice substituted by $C_1$-$C_{18}$alkyl, especially twice substituted, for example 2,6 diisopropylphenyl.

$C_7$-$C_{10}$aralkyl is for example benzyl, phenylpropyl, α,α-dimethylbenzyl or α-methylbenzyl.

$C_2$-$C_{18}$alkyl interrupted by at least one O atom is for example —$CH_2$—$CH_2$—O—$CH_2$—$CH_3$, —$CH_2$—$CH_2$—O—$CH_3$ or —$CH_2$—$CH_2$—O—$CH_2$—$CH_2$—$CH_2$—O—$CH_2$—$CH_3$. It is preferably derived from polyethylene glycol. A general description is —(($CH_2)_a$—O)$_b$—H/$CH_3$, wherein a is a number from 1 to 6 and b is a number from 2 to 10.

$R_{100}$ and $R_{101}$ form together with the carbon to which they are attached a mono or polycyclic C3-C18 carboxylic ring.

Non limiting examples of the resulting cycloalkylidenes $R_{101}R_{102}C$= are cyclobutylidene, cyclopentylidene, cyclohexylidene, cycloheptylidene, cyclooctylidene, cyclononylidene, cyclodecylidene, cycloundecylidene, cyclododecylidene, 4-methylcyclohexylidene, 3,3,5,5-tetramethylcyclohexylidene, 3,3,5-trimethylcyclohexylidene, 2,3-benzocyclohexylidene, 3,4-benzocyclohexylidene.

$R_{100}$ and $R_{101}$ form together with the carbon to which they are attached a mono or polycyclic or $C_1$-$C_{18}$ heterocyclic ring.

Non limiting examples of the resulting cycloalkylidenes $R_{101}R_{102}C$= are: 3-azacyclopentylidene, 3-oxacyclopentylidene, 2-methyl-3-oxacyclopentylidene, 4-azacyclohexylidene, 3,3,5,5-tetramethyl-4-azacyclohexylidene, 4-thiacyclohexylidene, 4-oxacyclohexylidene, The term "di, tri, or tetra $C_1$-$C_{18}$alkylidene" (when n is greater than 1) refers to a straight or branched carbon chain that may be fully saturated or have one or more units of unsaturation and has two points, three points or four points of attachment to the rest of the molecule.

The term "diacyl", means having two carbonyl or thiocarbonyl groups bonded to a radical selected from, for example, alkylene, alkenylene, alkynylene, haloalkylene, alkoxyalkylene, aryl, heterocyclyl, heteroaryl, aralkyl, cycloalkyl, cycloalkylalkyl, and cycloalkenyl. Examples of "diacyl" are phthaloyl, terephthaloyl, isophthaloyl, malonyl, succinyl, adipoyl, and the like.

Examples of "triacyl" are residues derived from citric acid or from trimesic acid.

Examples of "tetracyls" are residues derived from naphthaleneteteacarboxylic acid, benzophenone-tetracarboxylic acid.

Salts of the O-imino-isoureas are for example $HBF_4$, perchlorate, hydrochloride, sulfate, hydrogensulfate, alkylsulfonate, arylsulfonate or carboxylate salts.

In one embodiment n is 1 resulting in the use of O-Imino-isoureas compounds of the general formula (I) as source of radicals

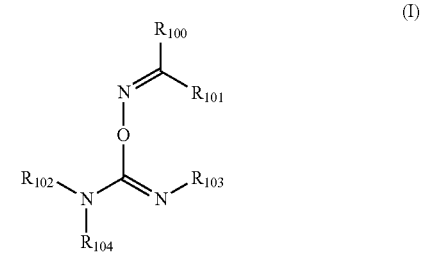

(I)

wherein $R_{100}$ and $R_{101}$ are independently H, $C_{1-18}$ alkyl, $C_3$-$C_{12}$cycloalkyl, $C_6$-$C_{14}$aryl, $C_1$-$C_{14}$heteroaryl, $C_7$-$C_{15}$aralkyl, $C_2$-$C_{14}$heteroaralkyl, cyano, or $R_{100}$ and $R_{101}$ form together with the carbon to which they are attached a mono or polycyclic $C_3$-$C_{18}$ carbocyclic or $C_1$-$C_{18}$ heterocyclic ring;

$R_{102}$ and $R_{103}$ are independently $C_1$-$C_{18}$alkyl, $C_3$-$C_{12}$cycloalkyl, $C_6$-$C_{14}$aryl, $C_6$-$C_{14}$aryl once or more than once substituted by $C_1$-$C_{18}$alkyl; $C_7$-$C_{15}$aralkyl, ($CH_3)_3$Si—; or $R_{102}$ and $R_{103}$ are $C_1$-$C_{18}$alkyl, $C_3$-$C_{12}$cycloalkyl, $C_6$-$C_{14}$aryl, $C_7$-$C_{15}$aralkyl or $R_{102}$ and $R_{103}$ are $C_1$-$C_{18}$alkyl, $C_3$-$C_{12}$cycloalkyl which are interrupted or substituted by O or by N containing groups selected from $C_1$-$C_{18}$alkylamino, bis($C_1$-$C_{18}$alkyl)amino or tris($C_1$-$C_{14}$alkyl)ammonium;

$R_{104}$ is H, $C_3$-$C_{12}$cycloalkyl, $C_7$-$C_{14}$aralkyl, $C_6$-$C_{14}$aryl or acyl selected from the group consisting of the following acyls —C(=O)—H, —C(=O)—$C_1$-$C_{18}$alkyl, —C(=O)—$C_2$-$C_{18}$alkenyl, —C(=O)—$C_6$-$C_{14}$aryl, —C(=O)—$C_2$-$C_{18}$alkenyl-$C_6$-$C_{14}$aryl, —C(=O)—O—$C_1$-$C_{18}$alkyl, —C(=O)—O—$C_6$-$C_{14}$aryl, —C(=O)—NH—$C_1$-$C_{18}$alkyl, —C(=O)—NH—$C_6$-$C_{14}$aryl and —C(=O)—N($C_1$-$C_{18}$alkyl)$_2$; or $R_{102}$ and $R_{104}$ form together with the nitrogen atom to which they are attached a 5 to 12 membered ring which my contain additional heteroatoms;

and salts thereof.

Preferences

In one embodiment n of formula I is 1.

In one embodiment n of formula I is greater than 1.

A preferred embodiment of the invention provides the use of compounds of the formula I wherein n is 1, as source of radicals, and wherein $R_{100}$ and $R_{101}$ are independently H, $C_{1-18}$ alkyl, $C_5$-$C_{12}$cycloalkyl, $C_6$-$C_{14}$aryl, $C_1$-$C_{14}$heteroaryl, $C_7$-$C_{15}$aralkyl, or $R_{100}$ and $R_{101}$ form together with the carbon to which they are attached a $C_5$-$C_{12}$ carbocyclic ring;

$R_{102}$ and $R_{103}$ are independently $C_1$-$C_4$alkyl, $C_5$-$C_{12}$cycloalkyl, $C_6$-$C_{14}$aryl, $C_6$-$C_{14}$aryl once or more than once substituted by $C_1$-$C_{18}$alkyl; $C_7$-$C_{15}$aralkyl;

$R_{104}$ is H, $C_1$-$C_{18}$alkyl, $C_5$-$C_{12}$cycloalkyl, $C_7$-$C_{14}$aralkyl, $C_6$-$C_{14}$aryl or acyl selected from the group consisting of the following acyls —C(=O)—H, —C(=O)—$C_1$-$C_{18}$alkyl, —C(=O)—$C_2$-$C_{18}$alkenyl, —C(=O)—$C_6$-$C_{14}$aryl; or $R_{102}$ and $R_{104}$ form together with the nitrogen atom to which they are attached a 5 to 6 membered ring;

Another preferred embodiment of the invention provides the use of compounds of the formula I wherein n is 1, as source of radicals, and wherein $R_{100}$ and $R_{101}$ are independently $C_{1-18}$ alkyl, $C_5$-$C_{12}$cycloalkyl, $C_6$-$C_{14}$aryl, $C_1$-$C_{14}$heteroaryl, $C_7$-$C_{15}$aralkyl or $R_{100}$ and $R_{101}$ form together with the carbon to which they are attached a $C_5$-$C_{12}$ carbocyclic ring;

$R_{102}$ and $R_{103}$ are independently $C_1$-$C_4$alkyl, cyclohexyl, $C_6$-$C_{14}$aryl; $C_6$-$C_{14}$aryl once or more than once substituted by $C_1$-$C_{18}$alkyl;

$R_{104}$ is H, $C_1$-$C_{18}$alkyl, $C_5$-$C_{12}$cycloalkyl, —C(=O)—$C_1$-$C_{18}$alkyl; or $R_{102}$ and $R_{104}$ form together with the nitrogen atom to which they are attached a 5 to 6 membered ring, and salts thereof Exemplified is the use of O-imino-isoureas compounds of the general formula (I) as source of radicals wherein $R_{100}$ and $R_{101}$ are independently $C_{1-18}$ alkyl, phenyl or $R_{100}$ and $R_{101}$ form together with the carbon to which they are attached a $C_5$-$C_{12}$ cycloalkyl ring.

$R_{102}$ and $R_{103}$ are independently $C_1$-$C_4$alkyl, $C_5$-$C_{12}$ cycloalkyl, $C_6$-$C_{14}$aryl; $C_6$-$C_{14}$aryl once or more than once substituted by $C_1$-$C_6$alkyl;

$R_{104}$ is hydrogen or —C(=O)—$C_1$-$C_{18}$alkyl.

and salts thereof.

In one embodiment the invention provides the use of compounds of formula I wherein n is 2, 3 or 4 as source of radicals, and wherein $R_{100}$ and $R_{101}$ are independently $C_{1-18}$ alkyl, phenyl or $R_{100}$ and $R_{101}$ form together with the carbon to which they are attached a $C_5$-$C_{12}$ cycloalkyl ring.

$R_{102}$ and $R_{103}$ are independently $C_1$-$C_4$alkyl, $C_5$-$C_{12}$ cycloalkyl, $C_6$-$C_{14}$aryl; $C_6$-$C_{14}$aryl once or more than once substituted by $C_1$-$C_6$alkyl;

$R_{104}$ is di-, tri-, tetra-$C_1$-$C_{18}$alkylidene, diacyls, triacyls or tetraacyls, and salts thereof Novel O-Imino-isourea compounds The invention further relates to novel O-imino-isoureas of the formula I'

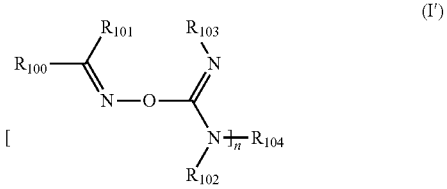

wherein n is 1, 2, 3 or 4, $R_{100}$, $R_{101}$, $R_{102}$, $R_{103}$ and $R_{104}$ are as defined above, and salts thereof;

with the proviso that the following compounds are excluded

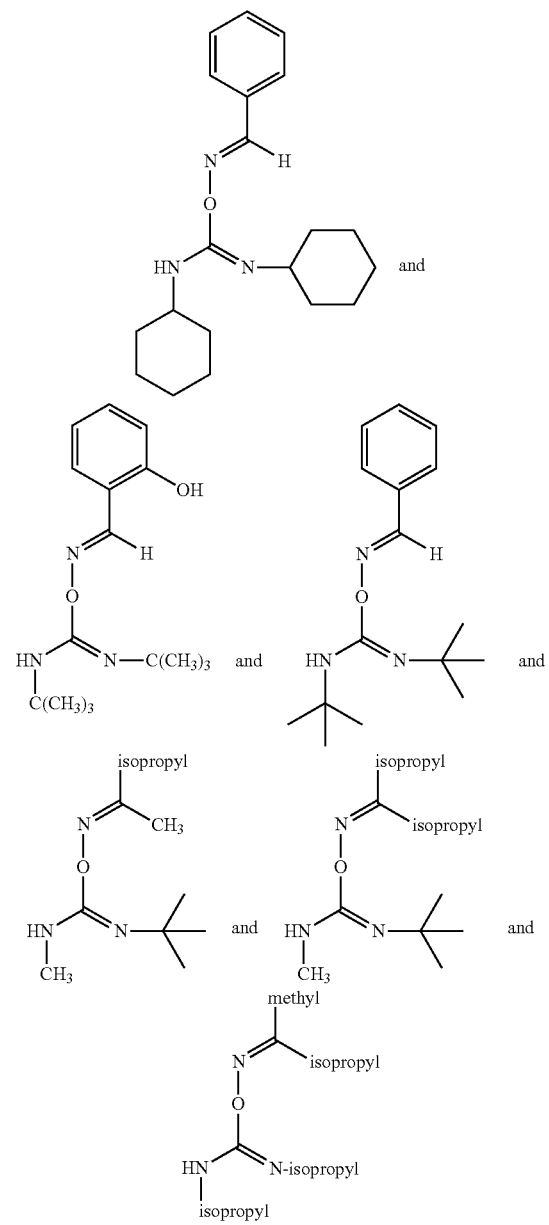

and the following O-Imino-isoureas derived from Ketoximes

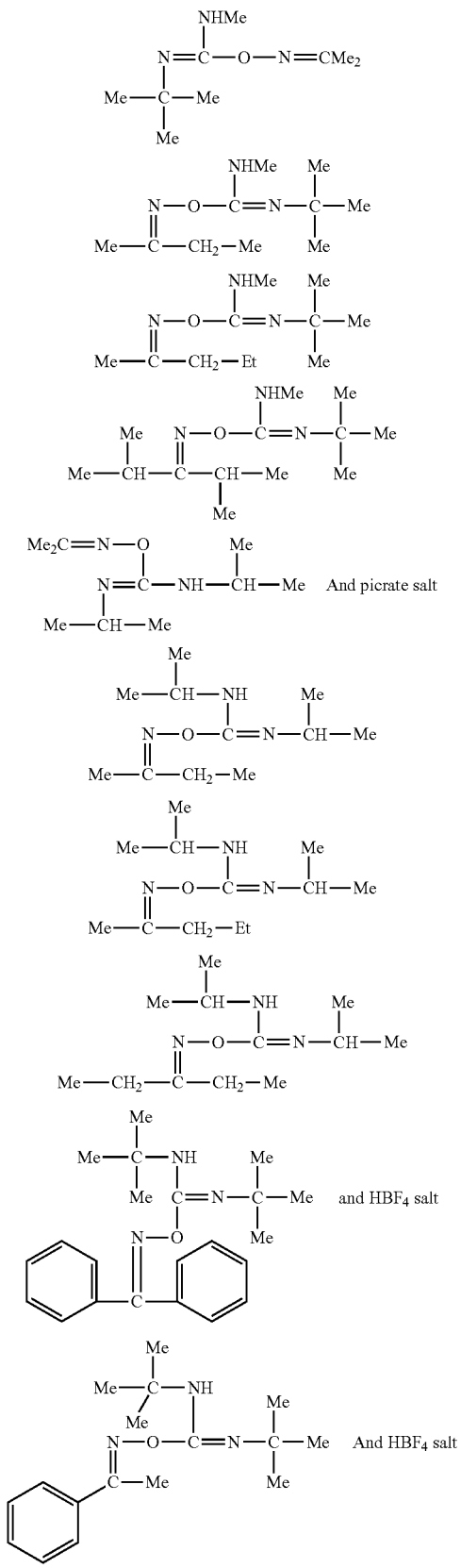

Concerning the novel compounds the compounds described by M. Radau and K. Hartke in "Archiv der Pharmazie" Vol. 305, 1972, pages 702-707 and described by Erich Schmidt et al. in "Justus Liebigs Annalen der Chemie" Vol. 639, 1961, pages 24-31 are disclaimed.

In one embodiment the invention further relates to novel O-imino-isoureas of the formula I' wherein n is 1

$R_{100}$, $R_{101}$, $R_{102}$, $R_{103}$ and $R_{104}$ are as defined above, and salts thereof;

with the proviso that the compounds listed above are excluded

Preferred novel O-imino-isoureas of the formula (I') correspond to those preferred compounds of the formula (I) listed above.

Preparation of the Inventive Compounds (I) or (I')

The compounds (I) with $R_{104}$=H are conveniently prepared via addition of aldoximes or ketoximes (II) to carbodiimides (III) according to the equation:

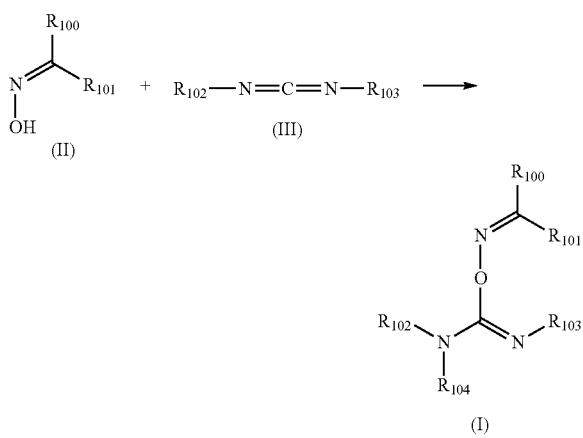

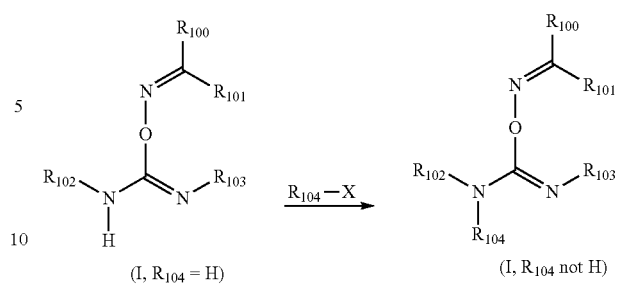

$R_{100}$, $R_{101}$, $R_{102}$ and $R_{103}$ are as defined above.

Additions of this type are described in the literature, e.g. by E. Schmidt, W. Carl.: Liebigs. Ann. Chem. 24, (639), 1961.

The addition can be conveniently performed by stirring the solution of (II) and (III) in an appropriate solvent such as for example ethyl acetate, toluene, dichloromethane, acetonitrile, tetrahydrofurane, hexane and the like. The reaction temperature can be room temperature (rt) or below, say −78° C., or above, say rt to 150° C.

Admixture of catalysts, for example Broensted acids such as HCl, p-TsOH, $HBF_4$ or $H_2SO_4$ or Lewis acids such as for example $BF_3$ or $Cu(O_3SCF_3)$ or bases, e.g. alkali metal hydroxides, alkoxides, amides or hydrides or amines such as e.g. triethylamine or DABCO or of amidines such as e.g. DBU or DBN may help improve the speed and yield of the addition of (II) to (Ill). Working under conditions of phase-transfer catalysis is an another option.

The oximes (II) and their preparation, for example via reaction of carbonyl compounds with hydroxylamine, is well known and does not need to be discussed. Moreover, many of them are commercially available Also many carbodiimides (III) are commercially available, e.g.

N,N'-Dicyclohexylcarbodiimide
1,3-Diisopropylcarbodiimide
Bis-(o-tolyl)-carbodiimide
Bis-(p-tolyl)-carbodiimide
Bis-(2,6-diisopropylphenyl)-carbodiimide-
Bis-(trimethylsilyl)-carbodiimide
1-sec-Butyl-3-ethyl carbodiimide
N-Cyclohexyl-N'-[4-(dimethylamino)-α-naphthyl]-carbodiimide
1-Cyclohexyl-3-(2-morpholinoethyl)-carbodiimide
1,3-Di-tert-butyl carbodiimide
1-Ethyl-3-(3-dimethylaminopropyl)-carbodiimide
1-Ethyl-3-(3-dimethylaminopropyl)-carbodiimide methiodide
Bis-(2,4,6-triisopropylbenzene)-carbodiimide The carbodiimides Ill may be also of oligomeric or polymeric.

Methods for preparation of carbodiimides bearing another substituents are well-known and described for example in: Henri Ulrich, "Chemistry and technology of carbodiimides", Wiley 2007.

The compounds (I) where $R_{104}$ is not H are conveniently prepared via alkylation or acylation of compounds (I) with $R_{104}$=H;

The suitable alkylation agents $R_{104}$—X are well known and comprise e.g. alkyl-, cycloalkyl- or aralkyl halides, sulfonates, triflates or trialkyloxonium salts.

The group $R_{104}$ can be introduced also via Michael addition of compounds I ($R_{104}$=H) to a suitable activated Michael acceptors such are e.g. acrylonitrile or alkyl acrylates.

The suitable acylation agents $R_{104}$—X are well known and comprise e.g. acyl halides or acyl anhydrides. Yet another possibility is the reaction of compounds I ($R_{104}$=H) with isocyanates.

The alkylation or acylation of compound (I, $R_{104}$=H) is optionally conducted in the presence of a base to neutralize the liberated acid H—X. Example of suitable bases are alkali hydroxides or alkali carbonates or amines such as triethylamine or pyridine.

Yet another possibility for synthesis of compounds (I) consists of reacting the oximes (II) with trisubstituted formamidines (IV).

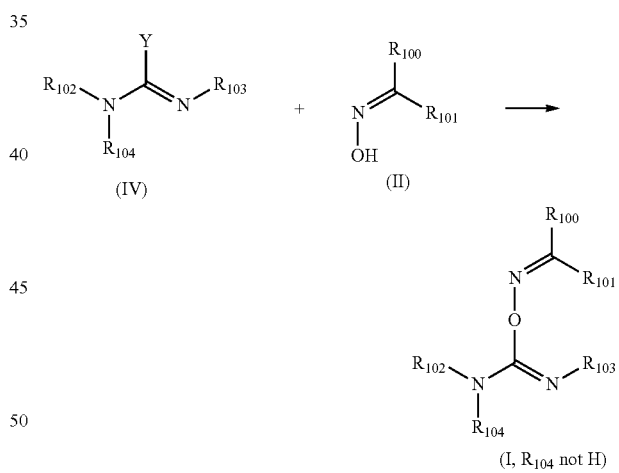

Y=Halogen, S-Alkyl, O-Alkyl

The formamidines (IV) are known compounds and are readily prepared from the corresponding trisubstituted ureas or thioureas. For example the preparation of chloroformamidines (IV, Y=Cl) is described by R. Appel, K. D. Ziehn, K. Warning.: Chemische Berichte 2093, 106(7), 1973.

The alkylthioformamidines (IV, Y=S-Alkyl) are readily obtained from trisubstituted thioureas as described by. e.g. Lecher & Graf.: Chemische Berichte 1328, 56, 1923.

Compounds of the formula (I) or (I') wherein n is greater than 1 are prepared by reacting a compound of formula (I) wherein n is 1 and $R_{104}$ is hydrogen with a di-, or tri-, or tetra carboxylic acid.

Use

These compounds are suitable as polymerization initiators, particularly for use in polymerization processes, since they allow the formation of particularly pure polymers and copolymers. The compounds are also suitable as polymerisation Initiators in dual cure processes where they are used in combination with photoinitiators.

The term polymer encompasses oligomers, cooligomers, polymers and copolymers, for example random block, multi-block, star or gradient copolymers.

A further advantageous property of the novel compounds in process technology is their suit-ability as additives in processes for lowering the molecular weight of polymers, in particular polypropylenes, and in processes for achieving a controlled increase in the molecular weight in particular in crosslinking of polyethylene.

Composition

The compounds of formula I or I' are present as polymerization auxiliaries or polymerization initiators in polymerizable compositions which comprise at least one ethylenically unsaturated, polymerizable monomer or oligomer.

The polymerization process initiated by the O-iminoisoureas can be triggered by different stimuli, for example by heat but also by electromagnetic radiation such as X-ray, ultraviolet, visible or infrared light or by actinic radiation such as for example β-radiation (electron beam).

Preferably a coating is prepared.

The invention therefore further provides a composition comprising
A) at least one ethylenically unsaturated, polymerizable monomer or oligomer; and
B) at least one compound of the formula I or I',
C) optionally a photoinitiator.

In one embodiment the photoinitiator is present. Any known photoinitiator can be used. Examples can be found e.g. in Crivello J. V., Dietliker K. K., (1999): Chemistry & Technology of UV & EB Formulation for Coatings, Inks & Paints, and in Bradley G. (ed.) Vol. 3: Photoinitiators for Free Radical and Cationic Polymerisation 2nd Edition, John Wiley & Son Ltd. Such compounds and derivatives are derived, for example, from the following classes of compounds: benzoins, benzil ketals, benzophenones, acetophenones, hydroxyalkylphenones, aminoalkylphenones, acylphosphine oxides, bisacylphosphine oxides, acylphosphine sulfides, bisacylphosphine sulfides acyloxyiminoketones, alkylamino-substituted ketones, such as Michler's ketone, peroxy compounds, dinitrile compounds, halogenated acetophenones, phenylglyoxylates, dimeric phenylglyoxalates, benzophenones, oximes and oxime esters, thioxanthones, coumarins, ferrocenes, titanocenes, onium salts, sulfonium salts, iodonium salts, diazonium salts, borates, triazines, bisimidazoles, polysilanes and dyes. It is also possible to use combinations of the compounds from the mentioned classes of compounds with one another and combinations with corresponding coinitiator systems and/or sensitisers.

The photopolymerisable compositions comprise the photoinitiator advantageously in an amount from 0.05 to 15% by weight, preferably from 0.1 to 8% by weight, based on the composition.

Preferably the compound of formula I or I' is present in an amount of from 0.01 to 10 weight-%, more preferably between 0.1 to 6 weight-% based on the weight of the unsaturated polymer(s) and monomer(s).

The compound A is present in an amount that the total amount is compounds A and B or A, B and C is 100% by weight.

Definition of the Ethylenically Unsaturated Compound:

The general radical-polymerizable compound is selected from known radical-polymerizable compounds having at least one ethylenically unsaturated double bond. Included are monomers, prepolymers, oligomers, a mixture thereof or a copolymer thereof.

Non-limiting examples of such monomers include: ethylenically unsaturated polymerizable monomers selected from the group consisting of alkenes, conjugated dienes, styrenes, acrolein, vinyl acetate, vinylpyrrolidone, vinylimidazole, maleic anhydride, acrylic acid, acrylic acid derivatives, vinyl halides and vinylidene halides.

Examples of alkenes and conjugated alkenes are ethylene, isoprene, 1,3-butadiene and $\alpha$-$C_5$-$C_{18}$alkenes.

Suitable styrenes may be substituted on the phenyl group by from one to three substituents selected from the group consisting of hydroxy, $C_1$-$C_4$alkoxy, e.g. methoxy or ethoxy, halogen, e.g. chlorine, amino and $C_1$-$C_4$alkyl, e.g. methyl or ethyl.

Unsaturated carboxylic acids such as (meth)acrylic acid, crotonic acid, itaconic acid (methylene succinic acid), maleic acid, or fumaric acid and salts, esters and amides thereof.

Also mentioned are unsaturated fatty acids such as linolenic acid and oleic acid. Acrylic and methacrylic acid are preferred.

It is also possible, however, to use saturated di- or polycarboxylic acids in admixture with unsaturated carboxylic acids. Examples of suitable saturated di- or poly-carboxylic acids include, for example, malonic acid, succinic acid, glutaric acid, adipic acid, sebacic acid, 1,4-cyclohexane dicarboxylic acid, tetrachlorophthalic acid, tetrabromophthalic acid, phthalic anhydride, tetrahydrophthalic acid, isophthalic acid, terepthalic acid, trimellitic acid, heptane-dicarboxylic acid, dodecanedicarboxylic acid, hexahydrophthalic acid, etc.

Esters of the above mentioned unsaturated acids are e.g. alkyl esters such as methyl, ethyl, 2-chloroethyl, N-dimethylaminoethyl, n-butyl, isobutyl-, pentyl, hexyl, cyclohexyl, 2-ethylhexyl, octyl, isobornyl[2-exobornyl] esters; or phenyl, benzyl or o-, m- and p-hydroxyphenyl esters; or hydroxy alkyl esters e.g. 2-hydroxyethyl, 2-hydroxypropyl, 4-hydroxybutyl, 3,4-dihydroxy-butyl or glycerol[1,2,3-propanetriol] esters, or epoxy alkyl esters e.g. glycidyl, 2,3-epoxybutyl, 3,4-epoxy butyl, 2,3-epoxycyclohexyl, 10,11-epoxyundecyl esters, or amino alkyl or mercapto alkyl esters, or esters as described below.

Amides of the above mentioned unsaturated acids are e.g. (meth)acryl amides, N-substituted (meth)acryl amides, e.g. N-methylolacrylamide, N-methylolmethacrylamide, N-ethylacryamide, N-ethylmethacrylamide, N-hexylacrylamide, N-hexylmethacrylamide, N-cyclohexylacrylamide, N-cyclohexylmethacrylamide-, N-hydroxyethylacrylamide, N-phenylacrylamide, N-phenylmethacrylamide, N-benzylacrylamide, N-benzylmetacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide, and N-(4-hydroxyphenyl)methacrylamide, IBMAA (N-isobutoxy-methyl acrylamide, or amides with aliphatic polyvalent amines.

(Meth)acrylnitriles;

Unsaturated acid anhydrides such as itaconic anhydride, maleic anhydride, 2,3-dimethyl maleic anhydride, and 2-chloromaleic anhydride.

Styrenes, such as methyl styrene, chloromethyl styrene, and o-, m-, and p-hydroxystyrene.

Vinyl ethers such as isobutyl vinyl ether, ethyl vinylether, 2-chloroethyl vinylether, hydroxyethyl vinylether, propyl vinylether, butyl vinylether, isobutyl vinyl ether, octyl vinylether and phenyl vinylether.

Vinyl esters such as vinyl acetate, vinyl chloroacetate, vinyl butyrate and vinyl benzoate.

vinyl chloride and vinylidene chloride

N-vinyl heterocyclic compounds, N-vinylpyrrolidone or suitably substituted vinylpyrrolidones, N-vinylcarbazol, 4-vinylpyridine, Further examples of esters are: diacrylate esters such as 1,6-hexane diol diacrylate (HDDA), ethylene glycol diacrylate, propylene glycol diacrylate, tripropylene glycol diacrylate, neopentyl glycol diacrylate, hexamethylene glycol diacrylate and bisphenol A diacrylate, divinylbenzene, divinyl succinate, diallyl phthalate, triallyl phosphate, triallyl isocyanurate and tris(2-acryloyl-ethyl) isocyanurate. trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetrameth-acrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

The following esters are also suitable: dipropylene glycol diacrylate, tripropylene glycol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Non limiting examples of higher molecular weight (oligomeric) polyunsaturated compounds (also known as prepolymers) are esters of ethylenically unsaturated mono- or polyfunctional carboxylic acids as described above and polyols or polyepoxides, and polymers having ethylenically unsaturated groups in the chain or in side groups, e.g. unsaturated polyesters, polyamides and polyurethanes and copolymers thereof, alkyd resins; polybutadiene and butadiene copolymers, polyisoprene and isoprene copolymers, polymers and copolymers having (meth)acrylic groups in side chains such as methacrylated urethanes and also mixtures of one or more such polymers.

Suitable polyols are aromatic and, especially, aliphatic and cycloaliphatic polyols. Examples of aromatic polyols are benzyl alcohol, hydroquinone, 4,4'-dihydroxydiphenyl, 2,2-di(4-hydroxy-phenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclo-pentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Aminoacrylates

A second oligomer used in combination with a monomer is an acrylate which has been modified by reaction with primary or secondary amines, as described, for example, in U.S. Pat. No. 3,844,916 of Gaske, in EP 280 222 of Weiss et al., in U.S. Pat. No. 5,482,649 of Meixner et al. or in U.S. Pat. No. 5,734,002 of Reich et al. Such amine-modified acrylates are also termed aminoacrylates. Aminoacrylates are obtainable, for example, under the name EBECRYL 80, EBECRYL 81, EBECRYL 83, EBECRYL P115, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley.

The unsaturated polymer can be used alone or in any desired mixtures.

Preparation of the Coating

The components of the formulation and optionally further additives are applied uniformly to a substrate by means of known coating techniques, for example by spin-coating, immersion, knife coating, curtain pouring, brush application or spraying, especially by electrostatic spraying and reverse-roll coating, and also by electrophoretic deposition. The quantity applied (coat thickness) and the nature of the substrate (layer support) are dependent on the desired field of application. The range of coat thicknesses generally comprises values from 0.1 μm to more than 300 μm.

Substrates

Suitable are substrates of all kinds, e.g. wood, textiles, paper, ceramics, glass, glass fibres, plastics such as polyester, polyethylene terephthalate, polyolefins or cellulose acetate, especially in the form of films, and also for metals such as Al, Cu, Ni, Fe, Zn, Mg or Co and GaAs, Si or $SiO_2$, to which there is to be applied a protective layer or an image by image-wise exposure.

Applications:

Liquid coating or powder coating or gelcoats. The coatings may be pigmented.

Also possible is the use in printing inks.

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of sterically hindered amines (HALS), e.g. of the 2-(2-hydroxyphenyl)-1,3,5-triazine or 2-hydroxyphenyl-2H-benzotriazole type. Examples of light stabilizers of the 2-(2- hydroxyphenyl)-1,3,5-triazine type are known from the patent literature, e.g. U.S. Pat. No. 4,619,956, EP-A-434 608, U.S. Pat. Nos. 5,198,498, 5,322,868, 5,369,140, 5,298,067, WO-94/18278, EP-A-704 437, GB-A-2,297,091 or WO-96/28431.

The compositions may further comprise other customary additives, e.g. fillers such as calcium carbonate, silicates, glass or glass fibre material, talcum, kaolin, mica, barium sulphate, metal oxides and hydroxides, carbon black, graphite, pulverized wood and pulverized or fibrous material from other natural products, synthetic fibres, plasticizers, lubricants, emulsifiers, pigments, fluidizers, catalysts, optical brighteners, flame retardants, antistatics or blowing agents.

The invention further provides a process for preparing the above-described oligomer, cooligomer, polymer or copolymer by free-radical polymerization using the above-described novel compounds of formula I or I'.

Free radical polymerisation includes thermal polymerisation and/or UV polymerisation.

Thermal polymerisation is thermal curing, IR-curing or NIR-curing

Thermal Curing:

Thermal curing refers to the application of convection heat or IR- or NIR-radiation after the mixture has been applied to substrate. In case of powder coatings the adhered powder coating is first melted to form a surface layer preferably by convection heat.

NIR-curing

The NIR radiation used in the process according to the invention is short-wave infrared radiation in the wavelength range from about 750 nm to about 1500 nm, preferably 750 nm to 1200 nm. Radiation sources for NIR radiation include, for example, conventional NIR radiation emitters, which are available commercially (for example, from Adphos).

IR-curing

The IR radiation used in the process according to the invention is medium wave radiation in the wave length range from about 1500 nm to about 3000 nm and/or longer-wave infrared radiation in the wave length range above 3000 nm.

IR radiation emitters of this kind are available commercially (for example, from Heraeus).

In a dual cure system the UV radiation may be followed by IR or NIR radiation or vice versa. Preferably the UV radiation follows the IR or NIR radiation. It is also possible that the UV radiation follows a convection heat exposure.

The invention further relates to a process for preparing an oligomer, a cooligomer, a polymer or a copolymer characterized in that the composition is subjected to the reaction conditions of free radical polymerization.

The invention further relates to a process for lowering the molecular weight of polypropylene, propylene copolymers or polypropylene blends characterized in defined in claim 1 or in claim 7 is added to the polypropylene, propylene copolymers or polypropylene blend and the mixture is heated.

The invention further relates to the use of the compounds of formula I or I' to prepare a coating.

The invention further relates to the use of the compounds of formula I or I' for crosslinking

PREPARATION EXAMPLES

The following Table 1 summarizes the prepared compounds.

TABLE 1

Examples of synthesized compounds (1)

| Nr | Structure |
|----|-----------|
| 1 | 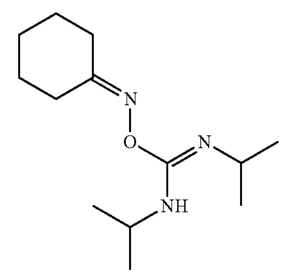 [SMILES: CC(C)/N=C(\NC(C)C)ON=C1CCCCC1] |
| 2 | 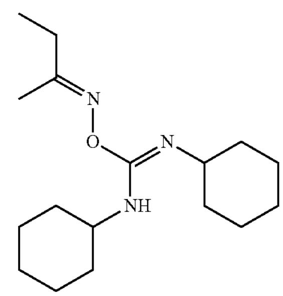 [SMILES: CC/C(C)=N/O/C(=N/C1CCCCC1)NC1CCCCC1] |
| 3 | 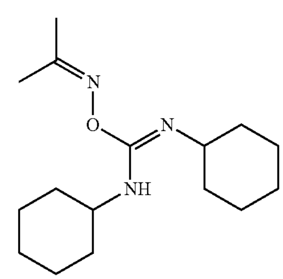 [SMILES: CC(C)=NO/C(=N/C1CCCCC1)NC1CCCCC1] |
| 4 | 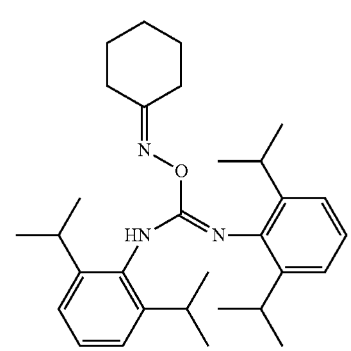 [SMILES: CC(C)c1cccc(C(C)C)c1/N=C(/Nc1c(C(C)C)cccc1C(C)C)ON=C1CCCCC1] |

TABLE 1-continued

Examples of synthesized compounds (1)

| Nr | Structure |
|----|-----------|
| 5 | 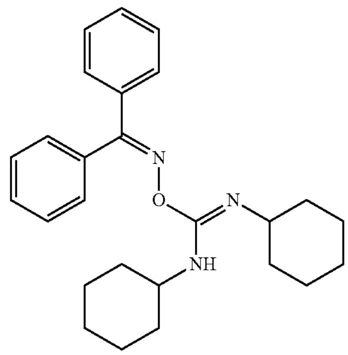 [SMILES: c1ccc(C(=NO/C(=N/C2CCCCC2)NC2CCCCC2)c2ccccc2)cc1] |
| 6 | 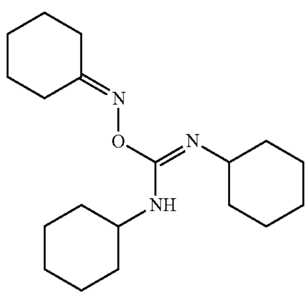 [SMILES: C1CCC(=NO/C(=N/C2CCCCC2)NC2CCCCC2)CC1] |
| 7 | 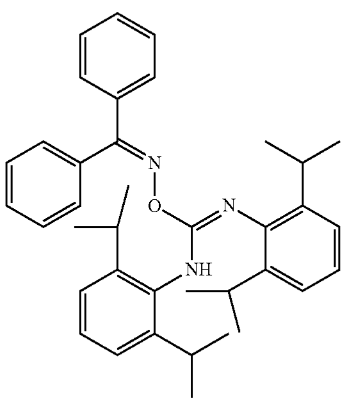 [SMILES: CC(C)c1cccc(C(C)C)c1/N=C(\Nc1c(C(C)C)cccc1C(C)C)ON=C(c1ccccc1)c1ccccc1] |
| 8 | 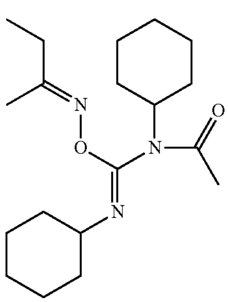 [SMILES: CC/C(C)=N/O/C(=N\C1CCCCC1)N(C(C)=O)C1CCCCC1] |
| 9 | |
| 10 | |
| 11 | |
| 12 | |

TABLE 1-continued

Examples of synthesized compounds (1)

| Nr | Structure |
|---|---|
| 13 | 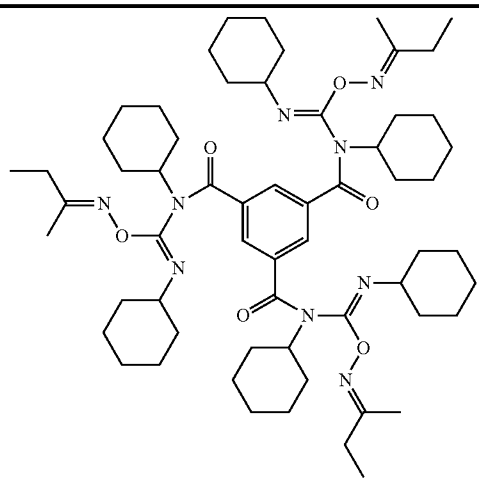 |
| 14 | 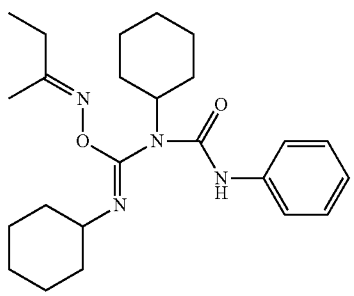 [SMILES: CC/C(C)=N/O/C(=N\C1CCCCC1)N(C(=O)Nc1ccccc1)C1CCCCC1] |
| 15 | 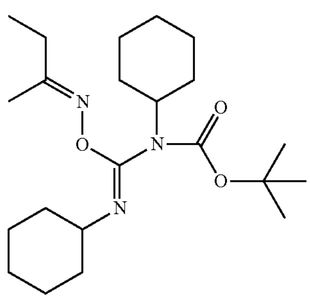 [SMILES: CC/C(C)=N/O/C(=N\C1CCCCC1)N(C(=O)OC(C)(C)C)C1CCCCC1] |
| 16 | 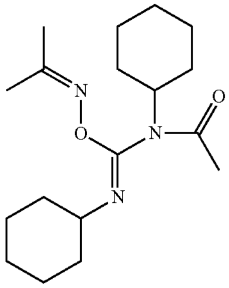 [SMILES: CC(=O)N(/C(=N/C1CCCCC1)ON=C(C)C)C1CCCCC1] |

Example 1

1,3-Diisopropyl-O—(N-cyclohexylideneamino)-isourea (Cmpd. 1)

To a solution of cyclohexanone oxime (5.65 g, 0.05 mol) in dry THF (40 ml) is added finely powdered NaOH (0.2 g) and diisopropylcarbodiimide (7.57 g, 0.06 mol). The mixture is then stirred 5 h at room temperature under argon. The turbid mixture is thereafter filtered and evaporated under reduced pressure to afford 11.75 g of a liquid which solidifies on standing to give the title compound as a slightly yellow solid, mp. 45-48° C.

ESI-MS for $C_{13}H_{25}N_3O$ (239.36) found $[M+1]^+$=239.8

$^1$H-NMR (CDCl$_3$, 300 MHz): 5.1-4.9 (bs, 1H, NH), 3.85-3.75 (m, 2H, CH-Me$_2$), 2.58-2.54 (m, 2H), 2.28-2.24 (m, 2H), 1.80-1.55 (m, 6H), 1.25-1.05 (m, 12H, CH-Me$_2$).

Example 2

1,3-Dicyclohexyl-O—(N-2-butylideneamino)-isourea (Cmpd. 2)

To a solution of methylethylketone oxime (4.6 g, 0.053 mol) in dry THF (30 ml) is added finely powdered NaOH (0.15 g) and dicyclohexylcarbodiimide (10.3 g, 0.05 mol). The mixture is then stirred 5 h at room temperature under argon. The turbid mixture is thereafter filtered and evaporated under reduced pressure. The residue is stirred 10 minutes with acetonitrile (30 ml), the acetonitrile phase is then discarded, the oily residue is dissolved in dichloromethane (30 ml), filtered and evaporated to afford 11.24 g of the title compound as a slightly yellow liquid.

ESI-MS for $C_{17}H_{31}N_3O$ (293.5) found $[M+1]^+$=294.0

$^1$H-NMR (CDCl$_3$, 300 MHz): 5.4-5.1 (bs, 1H, NH), 3.6-3.4 (m, 2H), 2.5-1.1 (m, 28H, residual aliphatic H).

Example 3

1,3-Dicyclohexyl-O—(N-isopropylideneamino)-isourea (Cmpd. 3)

To a solution of acetone oxime (3.65 g, 0.05 mol) in dry THF (35 ml) is added finely powdered NaOH (0.2 g) and dicyclohexylcarbodiimide (10.3 g, 0.05 mol). The mixture is then stirred 5 h at room temperature under argon. The turbid mixture is thereafter diluted with hexane (30 ml) filtered and evaporated under reduced pressure to afford 13.8 g of the title compound as a slightly yellow liquid.

ESI-MS for $C_{16}H_{29}N_3O$ (279.4) found $[M+1]^+$=280.1

$^1$H-NMR (CDCl$_3$, 300 MHz): 5.4-5.1 (bs, 1H, NH), 3.6-3.4 (m, 2H), 2.1-1.1 (m, 26 H, residual aliphatic H).

Example 4

1,3-Bis(2,6-diisopropylphenyl)-O—(N-cyclohexylideneamino)-isourea (Cmpd. 4)

To a solution of cyclohexanone oxime (1.13 g, 0.01 mol) in dry THF (25 ml) is added finely powdered NaOH (0.04 g) and bis(2,6-diisopropylphenyl)carbodiimide (3.65 g, 0.01 mol). The mixture is then stirred 4 h at room temperature under argon. The turbid mixture is thereafter filtered and evaporated under reduced pressure. The solid residue is crystallized from dichloromethane-hexane to afford 3.9 g of the title compound as a colorless solid, mp. 150-152° C.

Infusions-MS for $O_{31}H_{45}N_3O$ (475.5) found $[M+1]^+$=476

$^1$H-NMR (CDCl$_3$, 300 MHz): 7.4-6.8 (m, 6H, ArH), 3.6-3.4 (m, 2H), 3.2-3.0 (m, 2H), 2.3-2.1 (m, 4H), 1.8-1.1 (m, 30H, residual aliphatic H).

Example 5

1,3-Dicyclohexyl-O—(N-diphenylmethylideneamino)-isourea (Cmpd. 5)

To a solution of benzophenone oxime (3.94 g, 0.02 mol) in dry THF (40 ml) is added finely powdered NaOH (0.08 g) and dicyclohexylcarbodiimide (4.25 g, 0.0206 mol). The mixture is then stirred 22 h at room temperature under argon. The turbid mixture is thereafter filtered and evaporated under reduced pressure. The residue is crystallized from acetonitrile and again from acetonitrile-dichloromethane-hexane to afford 2.93 g of the title compound as a colorless solid, mp. 104-107° C.

ESI-MS for $C_{26}H_{33}N_3O$ (403.6) found $[M+1]^+$=403.8

$^1$H-NMR (CDCl$_3$, 300 MHz): 7.6-7.3 (m, 10H, ArH), 5.4-5.2 (bs, 1H, NH), 3.7-3.5 (m, 1H), 3.1-2.9 (m, 1H), 2.2-0.9 (m, 20H, residual aliphatic H).

Example 6

1,3-Dicyclohexyl-O—(N-cyclohexylideneamino)-isourea (Cmpd. 6)

To a solution of cyclohexanone oxime (5.65 g, 0.05 mol) in dry THF (30 ml) is added finely powdered NaOH (0.2 g) and dicyclohexylcarbodiimide (11.34 g, 0.055 mol). The mixture is then stirred 5 h at room temperature under argon. The turbid mixture is thereafter diluted with dichloromethane (25 ml), filtered and evaporated under reduced pressure. The residue is stirred 10 minutes with acetonitrile (30 ml), the acetonitrile phase is then discarded, the oily residue is dissolved in dichloromethane (30 ml), filtered and evaporated to afford 14.27 g of the title compound as a slightly yellow liquid.

ESI-MS for $C_{19}H_{33}N_3O$ (319.49) found $[M+1]^+$=320

$^1$H-NMR (CDCl$_3$, 300 MHz): 5.4-5.1 (bs, 1H, NH), 3.6-3.4 (m, 2H), 2.6-2.5 (m, 2H), 2.3-2.2 (m, 2H), 2.1-1.1 (m, 26H, residual aliphatic H).

Example 7

1,3-(2,6-Diisopropylphenyl)-O—(N-diphenylmethylideneamino)-isourea (Cmpd. 7)

A mixture of benzophenone oxime (1.97 g, 10 mmol), bis(2,6-diisopropylphenyl)carbodiimide (3.63 g, 10 mmol) and powdered NaOH (0.04 g) in dry THF (30 ml) is stirred 20 h at room temperature under argon. The mixture is thereafter evaporated and the residue is chromatographed on silica gel (hexanes-ethyl acetate 15:1) to afford 1.1 g of the title compound as a colorless glassy solid.

ESI-MS for $C_{38}H_{45}N_3O$ (559.80) found $[M+1]^+$=559.89
$^1$H-NMR (CDCl$_3$, 300 MHz): 7.5-6.7 (m, 16 ArH), 3.6-3.4 (m, 2H), 3.1-2.9 (m, 2H), 1.5-0.8 (m, 24H).

Example 8

1-Acetyl-1,3-dicyclohexyl-O—(N-2-butylideneamino)-isourea (Cmpd. 8)

To a solution of 1,3-dicyclohexyl-O—(N-2-butylideneamino)-isourea (Cmpd. 2) (10.5 g, 35.7 mmol) and 4-dimethylaminopyridine (100 mg) in pyridine (25 ml) is dropwise added acetanhydride (5 ml, 52.9 mmol). The mixture is stirred 2 h and evaporated. The residue is dissolved in toluene (100 ml), washed with water (5×20 ml), dried over MgSO$_4$ and evaporated to afford 9.58 g of the title compound as a light yellow oil.

$^1$H-NMR (CDCl$_3$, 300 MHz): mixture of isomers, 4.3-3.3 (m, 2H), 2.5-1.1 (m, 31H).

Example 9

1,3-dicyclohexyl-O—(N-cyclododecanylideneamino)-isourea (Cmpd. 9)

A mixture of cyclododecanone oxime (19.73 g, 100 mmol), dicyclohexylcarbodiimide (20.63 g, 100 mmol) and potassium-t-butylate (0.12 g) in hexane (75 ml) is stirred 23 h at 50° C. under argon. The mixture is then allowed to crystallize overnight at −18° C. The solid is filtered off and recrystallized from dichloromethane-hexane to afford 17.4 g of the title compound as white solid, mp. 108-111° C.

$^1$H-NMR (CDCl$_3$, 300 MHz): 3.6-3.4 (bs, 2H), 2.6-2.5 (m, 2H) 2.5-2.4 (m, 2H), 2.1-1.1 (m, 38H).
$^{13}$C-NMR (CDCl$_3$, 75.5 MHz): 163.22 (>C=N), 148.57 (O—C—(NH—)=N—).

Example 10

1-Pivaloyl-1,3-dicyclohexyl-O—(N-2-butylideneamino)-isourea (Cmpd. 10)

To a solution of 1,3-dicyclohexyl-O—(N-2-butylideneamino)-isourea (Cmpd. 2) (5.87 g, 20 mmol) and 4-dimethylaminopyridine (60 mg) in dichloromethane (25 ml) and triethylamine (3.1 ml, 22 mmol) is added pivaloyl chloride (2.46 g, 21 mmol). The mixture is stirred 43 h at room temperature, diluted with hexane (200 ml), washed with water (4×20 ml), dried over MgSO$_4$ and evaporated. The residue is chromatographed on silica gel (hexanes-ethyl acetate 4:1) to afford 5.49 g of the title compound as a colorless oil.

$^1$H-NMR (CDCl$_3$, 300 MHz): 4.2-4.0 (m, 1H), 3.6-3.5 (m, 1H), 2.5-1.0 (m, 2H), 2.1-1.1 (m, 28H), 1.20 (s, t-Bu).
$^{13}$C-NMR (CDCl$_3$, 75.5 MHz): 177.70 (t-Bu-CO), 163.12, 162.38 (>C=N, E, Z isomers), 146.53 (O—C—(NH—)=N—).

Example 11

1-Benzoyl-1,3-dicyclohexyl-O—(N-2-butylideneamino)-isourea (Cmpd. 11)

To a solution of 1,3-dicyclohexyl-O—(N-2-butylideneamino)-isourea (Cmpd. 2) (7.34 g, 25 mmol) and 4-dimethylaminopyridine (100 mg) in dichloromethane (25 ml) and triethylamine (3.9 ml, 27.5 mmol) is added benzoyl chloride (3.58 g, 25.5 mmol). The mixture is stirred 6 h at room temperature, diluted with hexane (200 ml), washed with water (4×20 ml), dried over MgSO$_4$ and evaporated. The residue is chromatographed on silica gel (hexanes-ethyl acetate 4:1) and the pure fractions are recrystallized from hexane to afford 7.2 g of the title compound as white crystals, mp 74-78° C.

$^1$H-NMR (CDCl$_3$, 300 MHz): 7.7-7.2 (m, 5 ArH), 4.5-4.3 (m, 1H), 3.6-3.4 (m, 1H), 2.6-1.0 (m, 28H).
$^{13}$C-NMR (CDCl$_3$, 75.5 MHz): 169.90 (Ph-CO), 163.56 (>C=N), 146.94 (O—C—(NH—)=N—).

Example 12

Terephthalic acid-bis-N-(1,3-dicyclohexyl-O—(N-2-butylideneamino)-isoure-1-yl)-amide (Cmpd. 12)

To a solution of 1,3-dicyclohexyl-O—(N-2-butylideneamino)-isourea (Cmpd. 2) (5.87 g, 20 mmol) and 4-dimethylaminopyridine (80 mg) in dichloromethane (25 ml) and triethylamine (2.8 ml, 20 mmol) is added terephthaloyl chloride (1.63 g, 8 mmol). The mixture is stirred 19 h at room temperature, diluted with dichloromethane (30 ml), washed with water (3×10 ml), dried over $MgSO_4$ and evaporated. The residue is chromatographed on silica gel (hexanes-ethyl acetate 3:1+5% $CH_2Cl_2$)) and the pure fractions are recrystallized from hexane to afford 3.97 g of the title compound as white crystals, mp 146-150° C.

$^1$H-NMR ($CDCl_3$, 300 MHz): 7.6-7.5 (m, 4 ArH), 4.5-4.3 (m, 2H), 3.6-3.4 (m, 2H), 2.2-1.0 (m, 56H).

$^{13}$C-NMR ($CDCl_3$, 75.5 MHz): 169.17 (OC-Ph-CO), 163.62 (>C=N), 146.69 (O—C—(NH—)=N—).

Example 13

Trimesic acid-tris-N-(1,3-dicyclohexyl-O—(N-2-butylideneamino)-isoure-1-yl)-amide (Cmpd. 13)

To a solution of 1,3-dicyclohexyl-O—(N-2-butylideneamino)-isourea (Cmpd. 2) (7.04 g, 24 mmol) and 4-dimethylaminopyridine (100 mg) in dichloromethane (25 ml) and triethylamine (3.35 ml, 24 mmol) is added trimesic acid chloride (1.6 g, 6 mmol). The mixture is stirred 20 h at room temperature, diluted with dichloromethane (80 ml), washed with water (4×20 ml), dried over $MgSO_4$ and evaporated. The residue is chromatographed on silica gel (hexanes-ethyl acetate 3:1) to afford 4.95 g of the title compound as a colorless resin.

$^1$H-NMR ($CDCl_3$, 300 MHz): 8.0-7.7 (m, 3 ArH), 4.3-4.1 (m, 3H), 3.5-3.3 (m, 3H), 2.4-1.0 (m, 84H).

$^{13}$C-NMR ($CDCl_3$, 75.5 MHz): 168.69 ($C_6H_3(CO)_3$), 163.83 (>C=N), 145.62 (O—C—(NH—)=N—).

Example 14

1-Phenylaminocarbonyl-1,3-dicyclohexyl-O—(N-2-butylideneamino)-isourea (Cmpd. 14)

To a solution of 1,3-dicyclohexyl-O—(N-2-butylideneamino)-isourea (Cmpd. 2) (2.93 g, 10 mmol) in dichloromethane (15 ml) is phenylisocyanate (1.19 g, 10 mmol). The mixture is stirred 1 h at room temperature and evaporated to afford 4.12 g of the title compound as a light yellow oil.

$^1$H-NMR ($CDCl_3$, 300 MHz): 7.6-7.1 (m, 5 ArH), 4.1-3.9 (m, 1H), 3.6-3.5 (m, 1H), 2.5-1.0 (m, 28H).

$^{13}$C-NMR ($CDCl_3$, 75.5 MHz): 164.22, 163.54 (>C=N, Isomers), 153.37 (PhNHCO), 149.75 (O—C—(NH—)=N—).

Example 15

1-t-Butyloxycarbonyl-1,3-dicyclohexyl-O—(N-2-butylideneamino)-isourea (Cmpd. 15)

To a solution of 1,3-dicyclohexyl-O—(N-2-butylideneamino)-isourea (Cmpd. 2) (5.87 g, 20 mmol) and 4-dimethylaminopyridine (125 mg) in dichloromethane (25 ml) is added di-t-butyl-dicarbonate (5.96 g, 27.3 mmol). The mixture is stirred 48 h at room temperature, diluted with methanol (2 ml), stirred for an additional hour and evaporated. The residue is chromatographed on silica gel (hexanes-ethyl acetate 3:1) to afford 5.3 g of the title compound as a colorless oil.

$^1$H-NMR ($CDCl_3$, 300 MHz): 3.9-3.3 (m, 2H), 2.4-1.0 (m, 28 H), 1.4 (s, t-Bu).

$^{13}$C-NMR ($CDCl_3$, 75.5 MHz): 161.78 (>C=N), 153.28, 152.96 (t-BuOCO, isomers), 145.28, 146.02 (O—C—(NH—)=N—, isomers).

Example 16

1-Acetyl-1,3-dicyclohexyl-O—(N-isopropylideneamino)-isourea (Cmpd. 16)

To a solution of 1,3-dicyclohexyl-O—(N-isopropylideneamino)-isourea (Cmpd. 3) (16.7 g, 60 mmol) and 4-dimethylaminopyridine (180 mg) in pyridine (40 ml) is added acetic anhydride (8.9 ml, 90 mmol). The mixture is stirred 2 h and then evaporated under reduced pressure. The residue is diluted with hexane (150 ml), washed with water (5×20 ml), dried over $MgSO_4$ and evaporated. The solid residue is recrystallized from hexane to afford 13.3 g of the title compound as white crystals, mp 74-78° C.

$^1$H-NMR ($CDCl_3$, 300 MHz): 4.2-4.0 (m, 1H), 3.7-3.3 (m, 1H), 2.1-1.0 (m, 29H).

$^{13}$C-NMR ($CDCl_3$, 75.5 MHz): 169.56, 169.35 ($CH_3$—CO), 161.83, 159.49 (>C=N), 146.52 (O—C—(NH—)=N—).

Polymerization Examples Using Selected Compounds From Table 1

Materials and Methods:

All solvents and monomers are distilled under argon or under reduced pressure via a Vigreux column shortly before use.

All reaction mixtures are freed of oxygen by purging with argon using the freeze/thaw technique and subsequently maintained under argon gas prior to the polymerization.

The reactants are in the form of a clear homogeneous solution before commencement of the polymerization reaction.

The monomer conversion is determined via $^1$H-NMR by integrating the signals of the polymer and unreacted monomer.

The polymers are characterized by GPC (gel permeation chromatography).

GPC: a two-piston production model pump RHEOS 4000 from FLUX INSTRUMENTS (represented by Ercatech AG, Bern, Switzerland) is used. The pump output is 1 ml/min. The chromatography is carried out on two Plgel 5 μm mixed-C columns from POLYMER INSTRUMENTS, Shropshire UK connected in series at 40° C. in THF. These columns are calibrated using polystyrene having $M_n$ values in the range from 200 to 2 000 000. The fractions are measured using an RI detector ERC-7515A from ERCATECH AG at 30° C.

Example 100

Polymerization of n-butyl acrylate using the Compound 4 at 120° C.

238 mg (0.5 mmol) of the compound 4 and 6.43 g (50 mmol) of n-butyl acrylate are placed in a 50 ml three-necked round-bottom flask provided with thermometer, condenser and magnetic stirrer and the mixture is degassed. The clear solution is heated 5 h to 120° C. under argon and then cooled to room temperature to afford a slightly yellow viscous polymer. Conversion of the monomer=77%, GPC: $M_n$=7796, $M_w$=58308.

Example 101

Polymerization of n-butyl acrylate using the Compound 5 at 100° C.

202 mg (0.5 mmol) of the compound 5 and 6.43 g (50 mmol) of n-butyl acrylate are placed in a 50 ml three-necked round-bottom flask provided with thermometer, condenser and magnetic stirrer and the mixture is degassed. The clear solution is heated 5 h to 100° C. under argon and then cooled to room temperature to afford a slightly yellow viscous polymer. Conversion of the monomer=72%, GPC: $M_n$=72491, $M_w$=143925.

Example 102

Polymerization of n-butyl acrylate using the compound 6 at 80° C.

319 mg (1 mmol) of the compound 6 and 12.85 g (100 mmol) of n-butyl acrylate are placed in a 50 ml three-necked round-bottom flask provided with thermometer, condenser and magnetic stirrer and the mixture is degassed. The clear solution is heated 5 h to 120° C. under argon and then cooled to room temperature to afford a colorless viscous polymer. Conversion=86%, GPC: $M_n$=9262, $M_w$=70597.

Example 103

Polymerization of a Coating Composition

The following unsaturated polymerizable composition is used (w/w %)

| | |
|---|---|
| Urethane-acrylate (Ebecryl 4858, UCB Chemicals/Cytec) | 50% |
| 1,6-Hexandiol diacrylate (UCB Chemicals/Cytec) | 30% |
| Tripropylene glycol diacrylate (UCB Chemicals/Cytec) | 20% |

1% of a compound (see Table 1) is dissolved in this composition and the resulting mixture is submitted to Differential scanning calorimetry (DSC) measurement. The activity of the tested compound is manifested by the exothermic curing reaction which is characterized by the Onset, Peak and Endset temperatures as well as the amount of heat liberated (exothermy).

The following DSC parameters are used:
Apparatus: DSC 30 (Mettler)
Temperature Gradient: 5° C./Min
Temperature Range: 30-300° C.
Measurement under Nitrogen, flow rate 5 ml/Min
Sample amount: approx. 10 mg compound in an aluminum cup The results summarized in the Table 2 show that no curing occurs with the blank formulation but that distinct exothermic curing is observed with the examples of the inventive compounds.

TABLE 2

DSC evaluation

| Compound from example | Onset [° C.] | Peak [° C.] | Endset [° C.] | Exothermy [J/g] |
|---|---|---|---|---|
| — (blank) | no | no | no | 0 |
| 1 | 50.72 | 68 | 82.08 | 239.74 |
| 2 | 60.00 | 75.60 | 110 | 315.60 |
| 3 | 64.27 | 76.44 | 85.33 | 245.88 |
| 4 | 73.43 | 80.99 | 84.90 | 244.25 |
| 5 | 75.04 | 86.05 | 93.91 | 237.99 |
| 6 | 53.07 | 60.61 | 66.28 | 220.37 |
| 8 | 91.82 | 106.83 | 121.38 | 368.60 |
| 9 | 71.98 | 79.93 | 86.51 | 314.78 |

Example 104

Determination of the Conversion of Double Bonds Via ATR-IR

A) Polymerization Between 2 PET Films

The acrylate formulation (0.2 g) was laminated between two PET films and then cured in an oven at 120° C. during 25 min. The conversion of double bonds was elucidated by ATR-IR (peak area at 810 cm$^{-1}$). The results are summarized in Table 3.

TABLE 3

Conversion of double bonds

| Compound from example | Concentration (%) | Remaining acrylate (%) |
|---|---|---|
| Acrylate Coatings system | 1 | 100 |
| Benzopinakol | 1 | 23.4 |
| 1 | 1 | 10.3 |
| 8 | 1 | 15.3 |
| 9 | 1 | 19.6 |

B) Polymerization on a White Coil Sheet

The acrylate formulation (0.2 g) was coated as a 200 μm thick film on a white coil sheet, then covered with a PET film and cured in an oven at 130° C. during 25 minutes. The conversion of double bonds was elucidated by ATR-IR (peak area at 810 cm$^{-1}$). The results are summarized in Table 4.

TABLE 4

Conversion of double bonds

| Compound from example | Concentration (%) | Remaining acrylate (%) |
|---|---|---|
| Acrylate Coatings system | 1 | 100 |
| Benzopinakol | 1 | 17.6 |
| 8 | 1 | 10.6 |
| 10 | 1 | 11.4 |
| 11 | 1 | 14.4 |
| 12 | 1 | 7.8 |
| 13 | 1 | 6.3 |
| 15 | 1 | 13.0 |
| 16 | 1 | 12.4 |

The invention claimed is:
1. An O-imino-isourea compound of formula I'

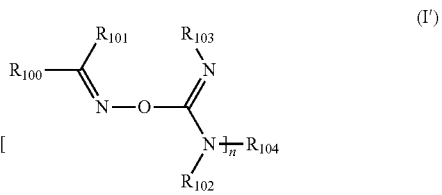

wherein:
n is 1, 2, 3 or 4;
$R_{100}$ and $R_{101}$ are each independently $C_{1-18}$alkyl, $C_3$-$C_{12}$cycloalkyl, $C_6$-$C_{14}$aryl, $C_1$-$C_{14}$heteroaryl, $C_7$-$C_{15}$aralkyl, $C_2$-$C_{14}$heteroaralkyl, Cyano, or $R_{100}$ and $R_{101}$ form together with a carbon to which they are attached a mono or polycyclic $C_3$-$C_{18}$ carbocyclic or $C_1$-$C_{18}$ heterocyclic ring;

$R_{102}$ and $R_{103}$ are each independently $C_1$-$C_{18}$alkyl, $C_3$-$C_{12}$cycloalkyl, $C_6$-$C_{14}$aryl, $C_6$-$C_{14}$aryl substituted with a $C_1$-$C_{18}$alkyl, $C_7$-$C_{15}$aralkyl, $(CH_3)_3Si$—; or $R_{102}$ and $R_{103}$ are $C_1$-$C_{18}$alkyl, $C_3$-$C_{12}$cycloalkyl, $C_6$-$C_{14}$aryl, $C_7$-$C_{15}$aralkyl, or $R_{102}$ and $R_{103}$ are $C_1$-$C_{18}$alkyl, $C_3$-$C_{12}$cycloalkyl which are interrupted or substituted by O or by N containing groups selected from the group consisting of $C_1$-$C_{18}$alkylamino, bis($C_1$-$C_{18}$alky)amino and tris($C_1$-$C_{14}$alkyl)ammonium;

$R_{104}$ if n is 1 is H, $C_1$-$C_{18}$alkyl, $C_3$-$C_{12}$cycloalkyl, $C_7$-$C_{14}$aralkyl, $C_6$-$C_{14}$aryl or acyl selected from the group consisting of —C(=O)—H, —C(=O)—$C_1$-$C_{18}$alkyl, —C(=O)—$C_2$-$C_{18}$alkenyl, —C(=O)—$C_6$-$C_{14}$aryl, —C(=O)—$C_2$-$C_{18}$alkenyl-$C_6$-$C_{14}$aryl, —C(=O)—O—$C_1$-$C_{18}$alkyl, —C(=O)—O—$C_6$-$C_{14}$aryl, —C(=O)—NH—$C_1$-$C_{18}$alkyl, —C(=O)—NH—$C_6$-$C_{14}$aryl and —C(=O)—N($C_1$-$C_{18}$alkyl)$_2$; or $R_{102}$ and $R_{104}$ if n is 1 form together with a nitrogen atom to which they are attached a 5 to 12 membered ring which optionally comprises an additional heteroatom, $R_{104}$ if n is more than 1 is di-, tri-, tetra-$C_1$-$C_{18}$alkylidene, diacyl, triacyl or tetraacyl and salts thereof, with the proviso that the following compounds are excluded

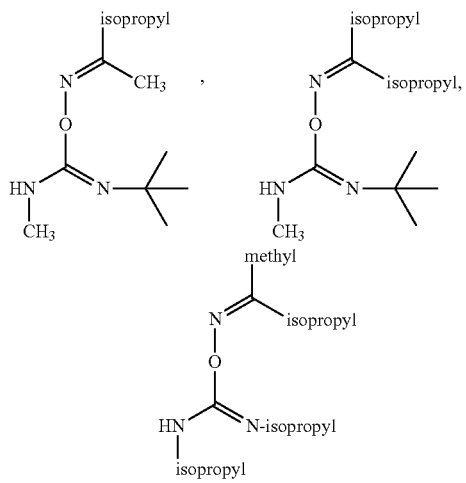

and the following O-Imino-isoureas derived from ketoximes:

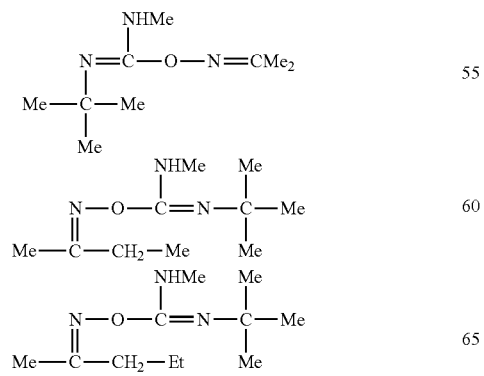

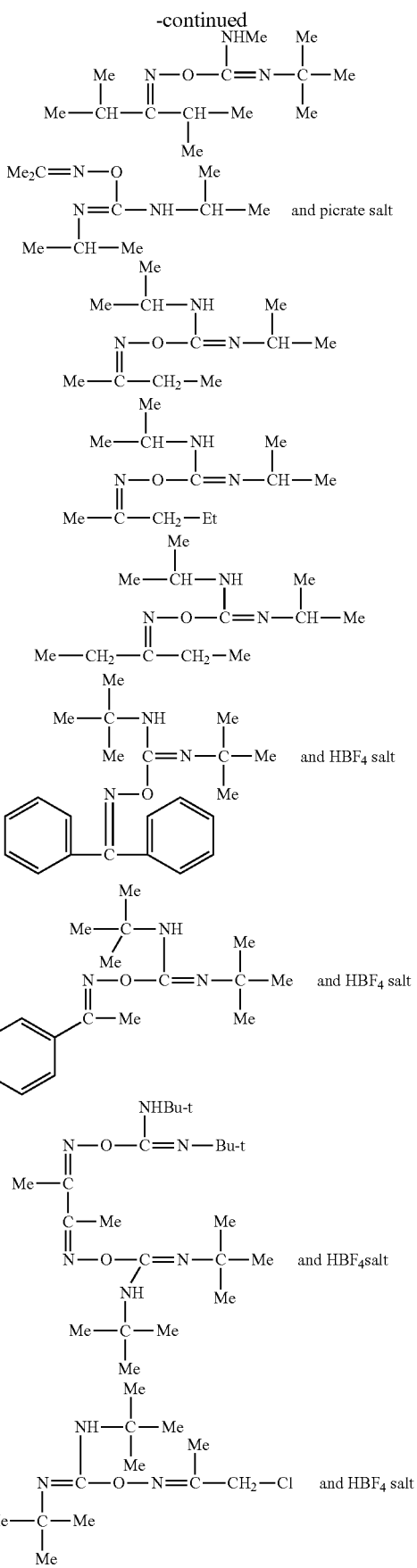

-continued

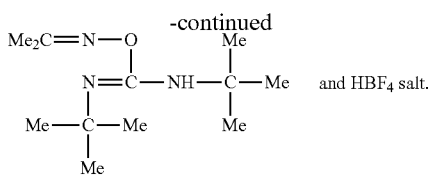 and HBF₄ salt.

2. The compound of claim 1, wherein n is 1.

3. A composition, comprising:
an ethylenically unsaturated, polymerizable monomer or oligomer;
a compound of the formula I' as defined in claim 1; and
optionally a photoinitiator.

4. A process for preparing an oligomer, a cooligomer, a polymer or a copolymer, comprising reacting the composition of claim 3 under conditions of free radical polymerization.

5. A coating process comprising:
applying a coating formulation comprising the compound of claim 1 to a substrate; and
polymerizing.

6. A crosslinking process, comprising heating a mixture comprising an unsaturated polymer resin and the compound of claim 1.

* * * * *